United States Patent [19]
Kimberly et al.

[11] Patent Number: 5,830,652
[45] Date of Patent: Nov. 3, 1998

[54] METHOD FOR DETERMINING PREDISPOSITION TO SEVERE FORMS OF AUTOIMMUNE DISEASE BY DETERMINING FCγ RECEPTOR ALLELIC PATTERNS

[75] Inventors: Robert P. Kimberly, Closter, N.J.; Jane E. Salmon, New York, N.Y.; Jeffrey C. Edberg, Englewood, N.J.

[73] Assignee: New York Society For The Ruptured And Crippled Maintaining The Hospital For Special Surgery, New York, N.Y.

[21] Appl. No.: 473,353

[22] Filed: Jun. 7, 1995

Related U.S. Application Data

[63] Continuation-in-part of Ser. No. 298,077, Aug. 30, 1994, abandoned.

[51] Int. Cl.$^6$ .............................. C12Q 1/68; C12P 19/34; C07H 21/04
[52] U.S. Cl. ........................... 435/6; 435/91.2; 536/24.3; 536/24.33; 935/6; 935/77; 935/78
[58] Field of Search ................................... 935/78, 77, 6; 536/23.12, 24.3, 24.31, 24.33; 436/506, 510; 435/6, 7.2, 7.21, 91.2

[56] References Cited

U.S. PATENT DOCUMENTS 5,219,728  6/1993  Khayat et al. ........................... 435/7.2

OTHER PUBLICATIONS

Osbourne et al. J. Immunol. Methods 173:207–217 (Aug. 1, 1994).
P.A. Ory et al. Sequences of complementary DNAs that encode NA1 and NA2 forms of Fc RIII on human neutrophils. J. Clin. Invest. Nov. 1989 vol. 84 p. 1688–1691.
B. Leaker and G. Cambridge "Clinical use of antineutrophil cytoplasmic antibodies" British Journal of Hospital Medicine Nov. 1993 50(9)540–8.
J.C. Jennette & R.J. Falk "Clinical and pathological classification of ANCA–associated vasculitis: What are the controversies?" 6th internation ANCA workshop Jul. 1995 In. Clincal and Exp. Immunol. 101(Supl):18–22.
Blasini et al., 1993, *Clinical and Experimental Immunology*, 94:423–428.
Barrett, 1983, *Textbook of Immunology*, Forth ed.: 277–281.
Joklik, 1984, *Zinsser Microbiology*, 18th ed.: 481.
Bredius et al., 1993, *Journal of Immunology*, 151:1463–1472.
Clark et al., 1991, *European Journal of Immunology*, 21:1911–1916.
Salmon et al., 1992, *J. Clin. Invest.*, 89:1274.
Frank et al., 1979, *N. Engl. J. Med.*, 300:518.
Fijen et al., 1993, *Ann. Int. Med.*, 119:636.
Saiki et al., 1988, *Science*, 239:487.
Maxam and Gilbert, 1977, *Proc. Natl. Acad. Sci. USA*.
Sanger et al., 1977, *Proc. Natl. Acad. Sci. USA*, 74:5463.
Chomocyznski et al., 1987, *Anal. Biochem.*, 162:156.
Gosselin et al., 1990, *J. Immunol.*, 144;1817Chehab et al., (1987), *Nature*, 329:293–294.
Biasini, AM et al., 1993, *Arthritis Rheum* 36:S195.
Porges et al., *Journal of Immunology*, 153:1271–1280, 1994.
Warmerdam et al., *Journal of Immunology*, 147:1338–1343, 1991.

*Primary Examiner*—W. Gary Jones
*Assistant Examiner*—Debra Shoemaker
*Attorney, Agent, or Firm*—Darby & Darby

[57] ABSTRACT

The present invention provides a method for determining whether a patient has a predisposition to develop severe forms of autoimmune disease. The method involves determining whether the Fcγ receptor allelic pattern of the patient corresponds most closely to known Fcγ receptor allelic patterns of patients having no autoimmune disease, mild autoimmune disease, or severe autoimmune disease. The invention also encompasses methods for determining if a patient has a predisposition to infection by certain encapsulated bacteria.

15 Claims, No Drawings

METHOD FOR DETERMINING PREDISPOSITION TO SEVERE FORMS OF AUTOIMMUNE DISEASE BY DETERMINING FCY RECEPTOR ALLELIC PATTERNS

This application is a continuation-in-part of U.S. patent application Ser. No. 08/298,077, filed Aug. 30, 1994 now abandoned.

FIELD OF THE INVENTION

This invention pertains to methods for assessing the relative susceptibility of human patient populations to autoimmune diseases in general, to severe forms of particular autoimmune diseases, and to infection by certain encapsulated bacteria.

BACKGROUND OF THE INVENTION

Fc receptors are membrane glycoproteins present on the surface of neutrophils, macrophages and other cell types, whose primary function is to bind and internalize immunoglobulins and immune complexes. Three distinct families of human receptors for the Fc domain of immunoglobulin G (IgG) have been identified on the basis of reactivity with monoclonal antibodies, cellular distribution, and cDNA sequences: FcγRI, FcγRII, and FcγRIII. Within each of these three Fcγ receptor families, distinct genes and alternative splice variants lead to a series of receptor isoforms that have striking differences in their extracellular, transmembrane, and intracellular regions. The salient features of the known classes of Fcγ receptors are compiled in Table 1.

Systemic lupus erythematosus (SLE) is a prototypic immune complex disease in which immune complexes, especially anti-DNA/DNA complexes, play an important role in pathogenesis. SLE-associated nephritis is characterized by high levels of anti-C1q autoantibodies, which are predominantly of the IgG2 subclass. SLE and other autoimmune diseases are characterized by a marked decrease in Fc receptor-mediated clearance by the mononuclear phagocyte system, the severity of which correlates with disease activity. In SLE, Fc receptor-mediated clearance of IgG-sensitized autologous erythrocytes (EA) is impaired (Frank et al., 1979, *N. Engl. J. Med.,* 300:518). It is likely that abnormal FcγRIIA function provides one basis for the disease-related defects and abnormal handling of IgG2-containing immune complexes in SLE.

Wegener's Granulomatosis is a multisystem disease characterized by inflammatory lesions, particularly of the upper and lower respiratory tract. The disease is associated with the presence of an IgG antibody directed against cytoplasmic constituents of neutrophils and monocytes, termed ANCA (anti-neutrophil cytoplasmic antibodies). ANCA are capable of triggering Fcγ receptor-mediated activation of immune cells, suggesting that this phenomenon plays a role in the pathogenesis of the disease.

When a patient is diagnosed with an autoimmune disease such as SLE or Wegener's granulomatosis, the choice of appropriate therapeutic interventions would be considerably facilitated by prognostic indicators that predict the future severity of the disease. However, to date it has not been possible to make such predictions with any level of accuracy based on some objective diagnostic criterion. Thus, there is

TABLE 1

| | Fcγ Receptor Families | | | | | | | |
|---|---|---|---|---|---|---|---|---|
| Structural Isoforms | FcγRI | | | FcγRII | | | Fcγ RIII | |
| Distinct genes | A | B | C | A | B | C | A | B |
| Splice variants | | + | (+) | a1, a2 | b1, b2, b3 | | | |
| Allelic variants | (+) | (+) | (+) | HR/LR | | | | NA1 NA2 |
| Membrane anchor | TM | TM | (TM) | a1:TM a2:secreted | TM | TM | γ/n/ζ complex | GPI |
| Cell Distribution | | | | | | | | |
| Neutrophils | (+) | | | + | | (?) | | + |
| Monocytes/Ø | + | | | + | (+) ~5% of donors | (?) | + | |
| Lymphocytes | | | | | B cells | (?) | NK cells | |

In addition to diversity based on distinct genes and their splice variants, different isoforms may also exhibit allelic polymorphisms. In several cases, the different alleles have been defined at the level of DNA sequence, and functional differences between the allelic forms have been noted. For example, the two recognized allelic forms of FcγRIIIB, NA1 and NA2, which differ by several amino acids and N-linked glycosylation sites, also differ in their capacity to mediate phagocytosis. In the case of FcγRIIA, the known allelic variants, HR ("high responder") and LR ("low responder"), which differ at amino acid position 131, differ substantially in their capacity to bind and internalize IgG2 (Salmon et al., 1992, *J. Clin. Invest.,* 89:1274). (In fact, FcγRIIA-LR is the only human FcγR that recognizes IgG2 efficiently.) Finally, allelic variants of FcγRI have also been found, though the possible functional significance of these sequence variations is not yet clear. It is likely that more than two allelic forms exist for each Fcγ receptor gene.

a need in the art for reliable diagnostic methods to identify patients with a higher probability of developing severe forms of autoimmune disease.

When humans are infected with encapsulated bacteria, such as *Haemophilus influenzae* and *Neisseria meningitidis,* the humoral immune response primarily involves production of specific IgG2 antibodies. Interestingly, Asian populations with a high frequency of FcγRIIA-LR have a very low incidence of *H. influenzae* infection. Conversely, among individuals with late complement component deficiencies, those homozygous for FcγRIIA-HR and FcγRIIIB-NA2 alleles are most likely to have a history of *N. meningitidis* infection (Fijen et al., 1993, *Ann. Int. Med.,* 119:636). These observations suggest that individuals with a higher risk of developing certain bacterial infections can be identified by analysis of their FcγRIIA and FcγRIIIB phenotypes.

SUMMARY OF THE INVENTION

The present invention provides a diagnostic method for determining predisposition to severe forms of autoimmune disease in a patient, comprising identifying the pattern of Fcγ receptor alleles encoded by the patients' DNA; comparing the pattern with the corresponding patterns of Fcγ receptor alleles in populations with no autoimmune disease, mild autoimmune disease, and severe autoimmune disease; and determining which of the corresponding patterns is most similar to the patient's allelic pattern. In one embodiment, the present invention provides a diagnostic method for determining predisposition to severe forms of Wegener's granulomatosis, comprising identifying the pattern of FcγRIIIB alleles in patients with Wegener's. In another embodiment, patients suffering from Wegener's granulomatosis are screened for RIIIB and RIIA genotypes. Identification of receptor alleles may be achieved immunologically, by isolating blood cells that express particular Fcγ receptors on their cell surface, and contacting the cells with antibodies that distinguish between different allelic forms of the receptor. Alternatively, DNA is isolated from the patient, and the presence of particular Fcγ receptor alleles is determined using gene amplification, followed by DNA sequencing, hybridization with allele-specific oligonucleotides, or single-stranded conformational polymorphism analysis.

The present invention also provides a diagnostic method for determining predisposition to infection with encapsulated bacteria, including *Haemophilus influenzae, Neisseria meningitidis,* and *Streptococcus pneumoniae,* comprising identifying the pattern of FcγRIIA and FcγRIIIB alleles encoded in the patient's DNA.

DETAILED DESCRIPTION OF THE INVENTION

All patent applications, patents, and literature references cited in this specification are hereby incorporated by reference in their entirety. In the case of inconsistencies, the present description, including definitions, will control.

Definitions:

1. "Allele" as used herein denotes an alternative version of a gene encoding the same functional protein but containing differences in its nucleotide sequence relative to another version of the same gene.

2. "Allelic polymorphism" as used herein denotes a variation in the nucleotide sequence within a gene, wherein different individuals in the general population may express different variants of the gene.

3. "Allelic pattern" as used herein denotes the two alleles in a patient encoding a particular gene i.e. homozygosity for a particular allele, or heterozygosity encompassing two different alleles. The term "allelic pattern" is used interchangeably with "genotype".

4. "Severe" autoimmune disease as used herein is defined as autoimmune disease encompassing clinical manifestations such as nephritis, vasculitis, or lung disease, or combinations thereof, that require aggressive treatment and may be associated with premature death.

5. "Amplification" of DNA as used herein denotes the use of polymerase chain reaction (PCR) to increase the concentration of a particular DNA sequence within a mixture of DNA sequences. For a description of PCR see Saiki et al., 1988, *Science,* 239:487.

6. "Chemical sequencing" of DNA denotes methods such as that of Maxam and Gilbert (Maxam-Gilbert sequencing, Maxam and Gilbert, 1977, *Proc. Natl. Acad. Sci. USA,* 74:560), in which DNA is randomly cleaved using individual base-specific reactions.

7. "Enzymatic sequencing" of DNA denotes methods such as that of Sanger (Sanger et al., 1977, *Proc. Natl. Acad. Sci. USA,* 74:5463), in which a single-stranded DNA is copied and randomly terminated using DNA polymerase.

The present invention provides a diagnostic method for screening patient populations to identify those individuals at risk for developing autoimmune disease in general, severe forms of particular autoimmune diseases, and infections caused by certain encapsulated bacteria. The method involves testing blood cells or DNA from individual patients for the presence of alternate alleles of different classes of Fcγ receptor genes, so as to identify a characteristic allelic pattern or genotype for one or more Fcγ receptor genes. In general, an individual's Fcγ receptor allelic pattern is compared with the distribution of allelic patterns in different test populations. Depending upon which Fcγ receptor forms are being analyzed, this screening can serve a variety of different diagnostic uses, which are described in more detail below.

The present invention also encompasses the identification of new allelic forms of Fcγ receptor genes, including FcγRI, RII, and RIII. Furthermore, the invention encompasses the establishment of statistically significant correlations, where they exist, between different allelic forms of Fcγ receptors (and allelic patterns formed by combinations of different alleles) and qualitative or quantitative aspects of particular autoimmune diseases e.g. the number, severity, and duration of symptoms, the need for medication or other ameliorative treatment, and the like.

The autoimmune diseases to which the methods of the present invention can be applied include without limitation systemic lupus erythematosus (SLE); systemic vasculitides such as Wegener's granulomatosis, polyarteritis nodosa, and cryoglobulinemic vasculitis; Sjogren's syndrome; mixed connective tissue disease; rheumatoid arthritis; and kidney diseases such as glomerulonephritis. The clinical manifestations of these diseases range from mild to severe.

Determination of Fcγ receptor genotypes according to the present invention may be performed in a susceptible population; alternatively, such testing can be performed after an initial diagnosis of autoimmune disease has been made. In this manner, different therapeutic interventions may be chosen for optimal long-term benefit. It will be understood that the particular Fcγ receptor allele that is screened for, the starting patient populations that are the targets of screening, and the test populations that provide the appropriate statistical database, will vary with the particular disease or syndrome. In one case, if a given Fcγ receptor allele is rare, but is found to be strongly associated with a particular syndrome, large-scale screening may be appropriate if early therapeutic intervention can reduce or ameliorate later development of symptoms. For example, if a patient is found to express an Fc receptor allele that is associated with increased risk of renal disease, the patient might be treated prophylactically with cyclophosphamide before substantial kidney damage has accumulated. Alternatively, a given Fcγ receptor allele may be common in the general population, and thus not be suitable for random screening. The same allele, however, when found in a patient suffering from a particular disease or syndrome, correlates with the subsequent development of more severe manifestations of the disease. In this case, identification of a patient's Fcγ receptor genotype according to the present invention is performed after an initial diagnosis of the disease.

Susceptibility to infection by encapsulated bacteria has been shown to be influenced by an individual's Fcγ receptor repertoire, in particular the presence of particular allelic forms of FcγRIIA. The infectious agents to which the methods of the present invention may be applied include without limitation *Haemophilus influenzae, Neisseria meningitidis, Streptococcus pneumoniae,* and other encapsulated bacteria. It is contemplated that identification of individuals homozygous for the FcγRIIA-HR allele will target these individuals for immunization against these infections. Furthermore, these individuals could be targeted for booster immunizations to insure that they achieve and maintain high levels of protective antibodies against these organisms.

In practicing the present invention, the presence of different Fcγ receptor alleles in an individual patient is determined by either: 1) immunological detection of the Fcγ receptor isoform itself present on the surface of appropriate immune cells ("phenotypic characterization"); or 2) molecular detection of the DNA or RNA encoding the Fcγ receptor isoform using nucleic acid probes, with or without nucleic acid sequencing ("genotypic characterization"). In the first embodiment, white blood cells are isolated from a patient to be tested for susceptibility to infection or severity of disease using methods that are standard and well known in the art e.g. gradient centrifugation or immunoadsorption (see Example 1 below). Antibodies that are capable of distinguishing between different allelic forms of a particular Fcγ receptor are then applied to the isolated cells to determine the presence and relative amount of each allelic form. The antibodies may be polyclonal or monoclonal, preferably monoclonal. Measurement of specific antibody binding to cells may be accomplished by any known method e.g. quantitative flow cytometry, or enzyme-linked or fluorescence-linked immunoassay. As detailed below for the analysis of FcγRIIA genotypes, the presence or absence of a particular allele, as well as the allelic pattern (i.e. homozygosity vs. heterozygosity) is determined by comparing the values obtained from a patient with norms established from populations patients of known gentoypes.

In an alternate embodiment, DNA is obtained from a patient, and the presence of DNA sequences corresponding to particular Fcγ receptor alleles is determined. The DNA may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, and tissue exudates at the site of infection or inflammation. DNA is extracted from the cell source or body fluid using any of the numerous methods that are standard in the art. It will be understood that the particular method used to extract DNA will depend on the nature of the source. The minimum amount of DNA to be extracted for use in the present invention is about 25 pg (corresponding to about 5 cell equivalents of a genome size of $4 \times 10^9$ base pairs).

Once extracted, the DNA may be employed in the present invention without further manipulation. Alternatively, the DNA region corresponding to all or part of a Fcγ receptor gene may be amplified by PCR. In this case, the amplified regions are specified by the choice of particular flanking sequences for use as primers. Amplification at this step provides the advantage of increasing the concentration of Fcγ receptor DNA sequences. The length of DNA sequence that can be amplified ranges from 80 bp to up to 30 kbp (Saiki et al., 1988, *Science,* 239:487). Preferably, primers are used that define a relatively short segment containing sequences that differ between different allelic forms of the receptor.

The presence of Fcγ receptor allele-specific DNA sequences may be determined by any known method, including without limitation direct DNA sequencing, hybridization with allele-specific oligonucleotides, and single-stranded conformational polymorphism (SSCP). Direct sequencing may be accomplished by chemical sequencing, using the Maxam-Gilbert method, or by enzymatic sequencing, using the Sanger method. In the latter case, specific oligonucleotides are synthesized using standard methods and used as primers for the dideoxynucleotide sequencing reaction.

Preferably, DNA from a patient is subjected to amplification by polymerase chain reaction (PCR) using specific amplification primers, followed by hybridization with allele-specific oligonucleotides. Alternatively, SSCP analysis of the amplified DNA regions may be used to determine the allelic pattern.

In an alternate embodiment, RNA is isolated from blood cells, using standard methods well known to those of ordinary skill in the art such as guanidium thiocyanate-phenol-chloroform extraction (Chomocyznski et al., 1987, *Anal. Biochem.,* 162:156.) The isolated RNA is then subjected to coupled reverse transcription and amplification by polymerase chain reaction (RT-PCR), using specific oligonucleotide primers. Conditions for primer annealing are chosen to ensure specific reverse transcription and amplification; thus, the appearance of an amplification product is diagnostic of the presence of one or both alleles. In another embodiment, RNA encoding Fcγ receptors is reverse-transcribed and amplified, after which the amplified Fcγ receptor-encoding cDNA is identified by hybridization to allele-specific oligonucleotides.

The present invention also encompasses the identification and analysis of new alleles of Fcγ receptor genes that may be associated with autoimmune diseases and other defects in IgG2-containing immune complex metabolism. In this embodiment, RNA encoding Fcγ receptors is selectively reverse-transcribed and amplified as described above. The DNA product is then sequenced directly, and the sequence compared with the sequence of the known alleles of the gene of interest. Once a new allele has been identified, monoclonal antibodies specific to the protein encoded by the new allele can be prepared by standard methods. These antibodies can then be used for screening of patient populations as described above.

In practicing the present invention, the distribution of Fc receptor allelic patterns in a large number (several hundred) patients with a particular autoimmune disease is determined by any of the methods described above, and compared with the distribution of Fc receptor allelic patterns in control (i.e. healthy) patients that have been matched for age and ethnic origin. A statistical method such as a 2×3 Chi square test is then used to determine whether the allele frequencies in the disease and normal groups are the same or different. In the case of SLE, the frequencies of the HR and LR alleles of FcγRIIA, and the NA1 and NA2 alleles of FcγRIIIB are tested in SLE patients and in normal populations. In the same patient cohort, the patient population is stratified by clinical manifestations. For example, SLE patients with nephritis and SLE patients without nephritis are compared for allele frequency. Finally, multiplex SLE families (i.e., families with more than one member with SLE) are studied to determine if the clinical marker (i.e. the presence of SLE) segregates with particular Fcγ receptor alleles.

In this manner, it is possible to obtain statistically significant correlations between a given pathological syndrome and previously known or novel Fcγ receptor alleles. It is contemplated that correlations between particular Fcγ receptor genotypes and particular diseases will provide an important prognosticator of disease susceptibility and clinical outcome. For example, there is a statistically significant correlation between the presence of FcγRIIA-HR homozygosity and the incidence of SLE in African-Americans (see Example 4 below.) Similarly, there is a statistically significant correlation between FcγRIIA-HR and renal disease in Caucasian SLE patients. In like manner, other Fcγ receptor genes may be used as predictive diagnostic indicators for SLE or other autoimmune diseases.

In one embodiment of the present invention, the DNA of patients with SLE is tested for the presence of the LR and HR alleles of the gene encoding FcγRIIA. In one approach, white blood cells e.g. neutrophils and monocytes are subjected to quantitative flow cytometry using, for example, monoclonal antibody (Mab) 41H.16, which recognizes the HR allele of human FcγRIIA, and Mab IV.3, which recognizes both HR and LR alleles (See Example 1 below). The ratio of fluorescence intensity of Mab 41H.16 and Mab IV.3 is measured, and compared with the values obtained from normalized groups of patients with known FcγRIIA phenotypes (Salmon et al., 1992, *J. Clin. Invest.*, 89:1274).

Any HR- or LR-specific monoclonal or polyclonal antibodies, as well as antibodies that recognize both HR and LR allelic forms of FcγRIIA, may be used in practicing the present invention. As described in Example 1 below, specific binding of a given antibody to blood cells is first tested in groups of patients with known FcγRIIA phenotypes, allowing the establishment of ranges of binding values for each antibody, and/or ratios of binding values for different antibodies, that correspond to HR homozygosity, LR homozygosity, or HR/LR heterozygosity. It will be understood by those of ordinary skill in the art that binding values, and ratios of binding values, are dependent on the particular method used to detect binding and must be normalized accordingly.

In an alternate approach, DNA is obtained from a patient suffering from SLE, and the presence of DNA sequences corresponding to the HR and LR alleles of FcγRIIA is determined. Preferably, primers are used to specifically amplify a sequence corresponding to amino acid residues 121–170 of the FcγRIIA protein sequence. The amplified product is then subjected to hybridization with allele-specific oligonucleotides, direct DNA sequencing, or SSCP (see Examples 2 and 3 below.

In a preferred embodiment of the present invention, the DNA of patients with Wegener's granulomatosis is tested for the presence of the NA1 and NA2 alleles of the gene encoding FcγRIIIB. Most preferably, olignucleotide primers are used to specifically amplify a sequence containing the polymorphic sites in Exon 3 of the RIIIB genomic sequence. The amplified product is then subjected to hybridization with allele-specific oligonucleotides, direct DNA sequencing, or SSCP (see Example 6 below).

The following working examples are intended to serve as non-limiting illustrations of the present invention.

Example 1

Determination of FcγRIIA Phenotype by Flow Cytometry

Fresh anticoagulated human peripheral blood was separated by centrifugation through a discontinuous two-step Ficoll-Hypaque gradient (Salmon et al., 1990, *J. Clin. Invest.*, 85:1287). Polymorphonuclear leukocytes (PMNs) were isolated from the lower interface and washed with HBSS (Gibco Laboratories, Grand Island, N.Y.). Contaminating erythrocytes were lysed with hypotonic saline (0.02% NaCl) for 20 seconds followed by 0.16% NaCl and a final wash with HBSS. Mononuclear cells were isolated from the upper interface and washed with HBSS.

Flow Cytometry:

Fresh blood cells were suspended at concentration of $5 \times 10^5$ cells/ml in phosphate-buffered saline (PBS) containing 0.1% (v/v) fetal bovine serum, and were incubated with saturating amounts of murine monoclonal antibody (Mab) 41H.16, which recognizes the HR allele of human FcγRIIA, and Mab IV.3, which recognizes both HR and LR alleles (Gosselin et al., 1990, *J. Immunol.*, 144:1817). Incubation with the primary antibodies was for 30 minutes at 4° C. After two washes with cold PBS containing 1% (v/v) fetal bovine serum, the cells were incubated with saturating amounts of phycoerythrin (PE)-conjugated goat anti-mouse IgG F(ab')2 (Tago, Inc., Burlingame, Calif.) for 30 minutes at 4° C., followed by two washes with cold PBS containing 1% fetal bovine serum. After staining, cell-associated immunofluorescence was quantified using a Cytofluorograf IIS (Becton Dickinson Immunocytometry Systems, Mountain View, Calif.). For each experiment, the instrument was calibrated with FITC-conugated calf thymus nuclei (Fluorotrol-GF, Becton, Dickinson and Co., Mountain View, Calif.) and quantitative PE microbead standards (Flow Cytometry Standards Corp., Research Triangle Park, N.C.) to allow assessment of both absolute and relative levels of immunofluorescence.

Mitogenesis Assay:

Blood cells isolated as described above were suspended at a concentration of $1 \times 10^6$ cells/ml in RPMI 1640 medium supplemented with 10% (v/v) fetal bovine serum, glutamine, penicillin, and streptomycin, and aliquoted into 96-well microtiter plates so that each well contained $1 \times 10^5$ cells. The following were added to triplicate wells: Antibody OKT3 (IgG2a anti-CD3, 5 μg/ml final concentration), antibody LEU4 (IgG1 anti-CD3, 5 μg/ml final concentration), non-specific control antibodies, or medium alone. The plates are incubated for 4 days at 37° C. 8 hours prior to the end of the incubation, 2 μCi of $^3$H-thymidine (Amersham, Arlington Heights, Ill.) were added to each well, and the incubation continued. Finally, the cells in each well were harvested, washed, and subjected to liquid scintillation counting.

Results:

Using the ratio of fluorescence intensity in both monocytes and PMNs, patients having a 41H.16/IV.3 ratio of 0.88–1.1 (n=8) were assigned a homozygous HR phenotype, those having a ratio of 0.42–0.59 (n=11) were assigned a heterozygous (i.e. HR/LR) phenotype, and those having a ratio of less than 0.13 (n=13) were assigned a homozygous LR phenotype. These assignments were corroborated by proliferation assays with anti-CD3 monoclonal antibodies of both murine IgG1 and IgG2a isotypes. In all cases, the results of the mitogenesis assays were in agreement with the flow cytometry assignment for human FcγRIIA.

Example 2

Determination of FcγRIIA Phenotype by DNA Amplification and Seguencing

DNA Isolation:

White blood cells were isolated from peripheral blood as described in Example 1. Genomic DNA was isolated from these cells using an automated nucleic acid extractor (Applied Biosystems, Foster City, Calif.).

PCR Amplification of the DNA Region Encompassing the FcγRIIA polymorphism:

Oligonucleotide primers were chosen that distinguish FcγRIIA from the highly homologous FcγRIIB and FcγRIIC genes. A sense primer from the second extracellular domain having the sequence: 5'-CAAGCCTCTGGTCAAGGTC-3' SEQ ID NO:1 was used, in conjunction with an antisense primer having the sequence 5'-GAAGAGCTGCCCATGCTG-3' SEQ ID NO:2, which is complementary to the downstream intron in which the sequences of FcγRIIA, RIIB, and RIIC diverge. The PCR product (278 base pairs) thus contains the sequence for codons 121–170 of the distal second extracellular FcγRIIA domain, the splice junction, and the proximal downstream intron.

Typically, 300 ng of genomic DNA is incorporated into a 100 μl reaction containing 200 pmol of each primer, 40 nmol of each deoxynucleotide triphosphate, and 1.7 units of Taq DNA polymerase, in a PCR reaction buffer (50 mM KCl; 10 mM Tris-HCl pH 8.3; 0.001% (w/v) gelatin; 1.5 mM $MgCl_2$). Thirty cycles of amplification are peformed in a DNA Thermal Cycler (Perkin-Elmer Cetus, Norwalk, Conn.), using the following protocol for each cycle: 94° C., 1 min; 55° C., 2 min; 72° C., 3 min. The resulting amplified products are then analyzed by electrophoresis in 1.5% agarose gels, followed by staining with ethidium bromide, according to standard procedures.

DNA Sequencing:

The PCR product described above is isolated from agarose gels using GeneClean II (Bio 101, La Jolla, Calif.), and subjected to automated DNA sequencing using dye-labelled dideoxynucleotide chain terminators (Applied Biosystems, Foster City, Calif.). DNA sequences are routinely determined from both strands, using sense or antisense primers, and reactions are analyzed on a laser-based, fluorescence-emission DNA sequencer (373A, Applied Biosystems.)

Example 3

Determination of FcγRIIA Phenotype by SSCP

Genomic DNA is isolated from white blood cells as described above. For SSCP analysis, 100 ng of this DNA is amplified as described above, with the following modifications: 100 ng of DNA are amplified in a 100 μl reaction mixture containing 5 pmol of each primer and 25 nmol of each deoxynucleotide triphosphate in the buffer described above. Thirty-eight cycles of amplification are performed, each cycle consisting of: 96° C., 15 sec; 50° C., 30 sec; and 72° C. 1 min.

0.65 μg of PCR product (typically present in 5.4–6.3 μl), were mixed with 10 μl gel loading buffer (95% (v/v) formamide, 0.05% (w/v) xylene cyanol, 20 mM EDTA), heated to 100° C. for 10 minutes, and placed immediately on wet ice. All subsequent steps are performed in a cold room at 4° C.

Samples are loaded onto a non-denaturing 8% (w/v) polyacrylamide gel in TBE (92 mM Tris, 95 mM borate, 2.5 mM EDTA) (18×24 cm, Hoefer SE 600, San Francisco, Calif.), with a 37.5:1 ratio of acrylamide:bisacrylamide. The gel apparatus is further cooled by the Hoefer SE 6160 heat exchanger, with a continuous flow of cool water surrounding the electrophoresis chamber. Electrophoresis was performed in a discontinuous buffer 925 mM Tris, 192 mM glycine) at 200 V for 6 hours. Following electrophoresis, DNA was detected by silver-staining of the gels (BioRad.)

For determination of FcγRIIA phenotype, the individual alleles are discriminated by their differential relative migration in the polyacrylamide gel.

Example 4

FcγRIIA is a Heritable Risk Factor for SLE in African-Americans

Genomic DNA was obtained from normal and SLE patients, and FcγRIIA-specific DNA amplification was carried out as described in Example 2. The amplified DNA was then separated on a 1% agarose gel and transferred to Hybond-N membranes (Amersham). The membranes were hybridized with oligonucleotides specific for the HR and LR alleles, i.e. 5'-ATTCTCCCGTTTGGATC-3' SEQ ID NO:3 (for HR) and 5'-ATTCCTCCCATTTGGATC-3' SEQ ID NO:4 (for LR), which had been 3'-end labelled with digoxigenin-11-ddUTP (Boehringer Mannheim Biochemicals). Blots were prehybridized for 2 hours in 5X SSC, 0.1% N-lauroylsarcosine, 0.02% SDS, 1% Blocking Reagent (Boehringer Mannheim) at 41° C. (HR) or 47° C. (LR) and then hybridized at the same temperature for 1 hour with the probes dilute in prehybridization solution to a concentration of 2 pmol/ml. Blots were washed twice at room temperature and twice at 42° C. The hybridized oligonucleotides were detected using an alkaline phosphatase-conjugated anti-digoxigenin antibody, which was visualized using a colorimetric substrate system consisting of nitroblue tetrazolium salt (NBT) and 5-bromo-4-chloro-3-indoyl phosphate (Boehringer Mannheim.)

TABLE 2

| | African - American | | | Caucasian | | | |
|---|---|---|---|---|---|---|---|
| | H/H | H/L | L/L | H/H | H/L | L/L | |
| SLE (253) | 37% | 47% | 16% | 25% | 53% | 22% | SLE (262) |
| NL (104) | 27% | 43% | 30% | 24% | 51% | 24% | NL (103) |

As shown in Table 2, the distribution of FcγRIIA alleles in Caucasian SLE patients was indistinguishable from controls. Notably, however, African-American SLE patients showed significant enrichment for HR homozygosity ($\chi^2$= 9.7, p<0.009 (2×3 table); odds ratio for SLE in non-LR homozygotes=2.26 (95% CL: 1.27 and 4.01)). This increase in homozygosity suggests that the presence of the HR allele is a novel risk factor contributing to SLE diathesis in African-Americans.

Example 5

FcγRIIA-HR Is Enriched in Patients with Renal Disease

Genomic DNA was isolated and amplified as described in Example 2, and subjected to hybridization with HR- and LR-specific oligonucleotides as in Example 4. As shown in Table 3 below, African-American SLE patients with nephritis exhibit a significantly higher proportion of HR/HR homozygosity than matched controls.

TABLE 3

| | HR/HR | HR/LR | LR/LR |
|---|---|---|---|
| SLE (nephritis) (115) | 38% | 50% | 11% |
| Disease-free (104) | 27% | 43% | 30% |

($X^2$ = 12.4; p < 0.003 (2 × 3 table); odds ratio for SLE nephritis in non-LR homozygotes: 3.33 (95% CL: 1.55 and 7.25)

Example 6

FcγRIIIB Alleles are Significantly Skewed in Wegener's Granulomatosis

Genomic DNA was obtained from normal individuals and those suffering from Wegener's granulomatosis. Amplification of FCγRIIIB DNA was carried out essentially as described in Example 2, using the following oligonucleotides as primers: 5'-GTGTTCCTGGAGCCTCAATG-3' SEQ ID NO:5 ("sense" primer) and 5'-ATGGACTTCTAGCTGCACC-3' SEQ ID NO:6 ("antisense" primer). Alternatively, amplification is carried out using 5'-GTGTTCCTGGAGCCTCAATG-3' SEQ ID NO:7 as the "sense" primer and 5'-GGACCACACATCATCTCATC-3' SEQ ID NO:8 as the "antisense" primer.

The amplified DNAs were then divided into five aliquots, which were bound to Hybond-N membranes (Amersham) in a "dot-blot" configuration. The membranes were then hybridized with oligonucleotides specific for the NA1 and NA2 alleles which were 3' end-labelled with digoxigenin-11-ddUTP (Boehringer Mannheim Biochemicals) prior to use. Hybridization was carried out as described in Example 4. The probes were as follows:

Probe #1: 5'-ATGGTACAGCGTGCTTGAGA-3' SEQ ID NO:9

Probe #2: 5'-CACAATGAGAACCTCATCTC-3' SEQ ID NO:10

Probe #3: 5'-CTGCCACAGTCAACGACAGT-3' SEQ ID NO:11

Probe #4: 5'-AGAAGTCCATGTCGGTGAGT-3' SEQ ID NO:12

Probe #5: 5'-AGTGTGACTCTGAAGTGCCA-3' SEQ ID NO:13

Probes #1 and #3 are specific for the NA2 allele, while probes #2 and #4 are specific for the NA1 allele. (Probe #5 reacts with human DNA irrespective of FcγRIIIB genotype.) Thus, if a positive signal was obtained only with probes #1 and #3, the individual was considered to be an NA1 homozygote; similarly, if a positive signal was obtained only with probes #2 and #4, the individual was considered to be an NA2 homozygote. Hybridization with probes #1–4 indicated that the individual was heterozygous for NA1 and NA2.

As shown in Table 4, the distribution of FcγRIIIB alleles is skewed in the Wegener's group. Enrichment for the NA1 allele (higher net function) and under-representation of the NA2 allele are evident in the WG group compared to normals (2×3 chi-square: $p<0.003$; 2×2 chi-square for allele frequency: $p<0.006$).

TABLE 4

|  | NA1/NA1 | NA1/NA2 | NA2/NA2 |
|---|---|---|---|
| Normals (N = 65) | 10 (15%) | 30 (46%) | 25 (38%) |
| Wegeners (N = 38) | 16 (42%) | 17 (45%) | 5 (13%) |

These results suggest that FcγRIIIB may play an important role in triggering polymorphonuclear leukocytes (PMNs) for tissue injury in Wegener's granulomatosis. Without wishing to be bound by theory, it is contemplated that screening of Wegener's patients for FcγRIIIB phenotype, in conjunction with monitoring of ANCA titers, will provide a sensitive prognosticator of incipient flare-up of disease symptoms.

What we claim is:

1. A diagnostic method for determining predisposition to severe forms of an autoimmune disease wherein said autoimmune disease is characterized by a Fcγ receptor mediated response in a patient suffering from an autoimmune disease, comprising
   (i) establishing a statistically significant correlation between the allelic pattern of one or more Fcγ receptor genes and severity of said autoimmune disease;
   (ii) identifying the corresponding Fcγ receptor allelic patterns of said patient;
   (iii) comparing the Fcγ receptor allelic patterns of said patient with the corresponding allelic patterns of humans with no autoimmune disease, mild forms of said autoimmune disease, and severe forms of said autoimmune disease; and
   (iv) determining which of said corresponding allelic patterns is most similar to the allelic pattern of said patient,
   wherein if the Fcγ receptor allelic pattern of said patient is most similar to the corresponding allelic pattern of human with severe forms of said autoimmune disease, said patient has a predisposition to severe forms of said autoimmune disease.

2. The method of claim 1, wherein said autoimmune disease is a member selected from the group consisting of systemic lupus erythematosus, systemic vasculitides, Sjogren's sydrome, mixed connective tissue disease, rheumatoid arthritis, and glomerulonephritis.

3. The method of claim 2, wherein said systemic vasculitis comprises Wegener's granulomatosis.

4. The method of claim 1, wherein said severe autoimmune disease is characterized by symptoms selected from the group consisting of nephritis, vasculitis, and lung disease.

5. The method of claim 1, which comprises identifying the alleles of FcγRIIIB of said patient.

6. The method of claim 5, wherein said FcγRIIIB alleles comprise the NA1 and NA2 alleles.

7. The method of claim 6, wherein said determining step comprises quantitative flow cytometry.

8. The method of claim 6, wherein said determining step comprises enzyme-linked immunoassay.

9. The method of claim 1, wherein said identifying comprises the steps of:
   (a) obtaining DNA from said patient; and
   (b) determining the sequence of polymorphic regions of genes encoding Fcγ receptors contained within said DNA.

10. The method of claim 1, wherein said identifying step comprises:
    (a) obtaining DNA from said patient;
    (b) amplifying regions of said DNA containing Fcγ receptor genes or fragments thereof;
    (c) hybridizing said amplified DNA with one or more allele-specific oligonucleotides; and
    (d) identifying the oligonucleotides that hybridize specifically with said DNA.

11. The method of claim 1, wherein said identifying step comprises:
    (a) obtaining white blood cells from said patient;
    (b) isolating RNA from said cells;
    (c) subjecting said RNA to coupled reverse transcription and amplification specified by Fcγ receptor allele-specific oligonucleotide primers, to produce Fcγ receptor-encoding DNA; and
    (d) determining the sequence of said DNA.

12. A diagnostic method for determining predisposition to severe forms of Wegener's granulomatosis in patients suffering from Wegener's granulomatosis, comprising
    (i) obtaining DNA samples from said patients;
    (ii) amplifying the regions of said DNA samples containing FcγRIIIB genes;
    (iii) individually hybridizing parallel samples of said amplified DNAs with oligonucleotides specific for the NA1 and NA2 alleles of said FcγRIIIB genes; and
    (iv) identifying the DNA samples that are homozygous for said FcγRIIIB NA1 allele,
    wherein the identification of a DNA sample as homozygous for said Fcγ RIIIB NA1 allele indicates that said patient has a predisposition to severe forms of Wegener's granulomatosis.

13. The method of claim 11, further comprising monitoring the titer of anti-neutrophil cytoplasmic antibodies in said patients.

14. The method of claim 11, further comprising identifying the alleles of FcγRIIA of said patient.

15. A diagnostic method for determining predisposition to severe forms of systemic lupus erythematosus (SLE) in patients suffering from SLE, comprising
    (i) obtaining DNA samples from said patients;
    (ii) amplifying the regions of said DNA samples containing FcγRIIA genes;
    (iii) individually hybridizing parallel samples of said amplified DNAs with oligonucleotides specific for the HR and LR alleles of said FcγRIIA genes; and
    (iv) identifying from among said DNA samples those homozygous for said FcγRIIA HR allele,
    wherein the identification of a DNA sample as homozygous for said Fcγ RIIA HR allele indicates that said patient has a predisposition to severe forms of SLE.

* * * * *

UNITED STATES PATENT AND TRADEMARK OFFICE
CERTIFICATE OF CORRECTION

PATENT NO. : 5,830,652
DATED : November 3, 1998
INVENTOR(S) : Robert P. KIMBERLY et al.

It is certified that error appears in the above-identified patent and that said Letters Patent is hereby corrected as shown below:

On the title page, item: [75], Inventors change "CLOSTER, N.J." to --BIRMINGHAM, ALABAMA--; change "ENGLEWOOD, NY" to --BIRMINGHAM, ALABAMA--.

Signed and Sealed this

Twentieth Day of April, 1999

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( v i i ) IMMEDIATE SOURCE:
        ( B ) CLONE: RIIA-sense ( x i ) SEQUENCE DESCRIPTION: SEQ ID NO:1:

C A A G C C T C T G    G T C A A G G T C                                                                                                  1 9

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
    ( A ) ORGANISM: Homo sapiens ( v i i ) IMMEDIATE SOURCE:
    ( B ) CLONE: RIIA-antisense ( x i ) SEQUENCE DESCRIPTION: SEQ ID NO:2:

GAAGAGCTGC CCATGCTG                18

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( v i i ) IMMEDIATE SOURCE:
        ( B ) CLONE: HR-specific ( x i ) SEQUENCE DESCRIPTION: SEQ ID NO:3:

ATTCTCCCGT TTGGATC                17

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Homo sapiens ( v i i ) IMMEDIATE SOURCE:
        ( B ) CLONE: LR-specific ( x i ) SEQUENCE DESCRIPTION: SEQ ID NO:4:

ATTCCTCCCA TTTGGATC                18

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Homo sapiens ( v i i ) IMMEDIATE SOURCE:
        ( B ) CLONE: RIIIB sense1

( x i ) SEQUENCE DESCRIPTION: SEQ ID NO:5:

GTGTTCCTGG AGCCTCAATG                20

( 2 ) INFORMATION FOR SEQ ID NO:6:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: DNA (genomic)

( v i ) ORIGINAL SOURCE:
  ( A ) ORGANISM: Homo sapiens ( v i i ) IMMEDIATE SOURCE:
  ( B ) CLONE: RIIIB antisense 1

( x i ) SEQUENCE DESCRIPTION: SEQ ID NO:6:

ATGGACTTCT AGCTGCACC                                                                 19

( 2 ) INFORMATION FOR SEQ ID NO:7:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Homo sapiens ( v i i ) IMMEDIATE SOURCE:
    ( B ) CLONE: RIIIB sense 2

( x i ) SEQUENCE DESCRIPTION: SEQ ID NO:7:

GTGTTCCTGG AGCCTCAATG                                                                20

( 2 ) INFORMATION FOR SEQ ID NO:8:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Homo sapiens ( v i i ) IMMEDIATE SOURCE:
    ( B ) CLONE: RIIIB antisense 2

( x i ) SEQUENCE DESCRIPTION: SEQ ID NO:8:

GGACCACACA TCATCTCATC                                                                20

( 2 ) INFORMATION FOR SEQ ID NO:9:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Homo sapiens ( v i i ) IMMEDIATE SOURCE:
    ( B ) CLONE: RIIIB probe 1

( x i ) SEQUENCE DESCRIPTION: SEQ ID NO:9:

ATGGTACAGC GTGCTTGAGA 20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Homo sapiens ( v i i ) IMMEDIATE SOURCE:
        ( B ) CLONE: RIIIB probe 2

( x i ) SEQUENCE DESCRIPTION: SEQ ID NO:10:

CACAATGAGA ACCTCATCTC 20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Homo sapiens ( v i i ) IMMEDIATE SOURCE:
        ( B ) CLONE: RIIIB probe 3

( x i ) SEQUENCE DESCRIPTION: SEQ ID NO:11:

CTGCCACAGT CAACGACAGT 20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Homo sapiens ( v i i ) IMMEDIATE SOURCE:
        ( B ) CLONE: RIIIB probe 4

( x i ) SEQUENCE DESCRIPTION: SEQ ID NO:12:

AGAAGTCCAT GTCGGTGAGT 20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Homo sapiens ( v i i ) IMMEDIATE SOURCE:

( B ) CLONE: RIIIB probe 5

( x i ) SEQUENCE DESCRIPTION: SEQ ID NO:13:

AGTGTGACTC TGAAGTGCCA                                                                          20